United States Patent
Schwieker

[11] Patent Number: 5,836,898
[45] Date of Patent: Nov. 17, 1998

[54] LITHOTRIPSY COMBINATION COMPRISING A THERAPY UNIT

[75] Inventor: Horst Schwieker, Hamburg, Germany

[73] Assignee: U.S. Philips Corporation, New York, N.Y.

[21] Appl. No.: 568,085

[22] Filed: Dec. 6, 1995

[30] Foreign Application Priority Data

Dec. 7, 1994 [DE] Germany ............... 44 43 495.2

[51] Int. Cl.⁶ .................................................. A61B 17/22
[52] U.S. Cl. ............................. 601/4; 378/205; 606/2.5; 600/439
[58] Field of Search ............................... 128/653.1; 601/2, 601/3, 4; 607/97; 378/205, 195–197; 600/407, 439; 606/2.5

[56] References Cited

U.S. PATENT DOCUMENTS

| | | | |
|---|---|---|---|
| 4,984,575 | 1/1991 | Uchiyama et al. | 128/660.03 |
| 5,029,826 | 7/1991 | Schaefer | 269/322 |
| 5,065,741 | 11/1991 | Uchiyama et al. | 128/24 EL |
| 5,178,135 | 1/1993 | Uchiyama et al. | 128/240 EL |
| 5,263,076 | 11/1993 | Elff et al. | 378/162 |
| 5,285,772 | 2/1994 | Rattner | 128/24 EL |
| 5,388,581 | 2/1995 | Bauer et al. | 128/653.1 |
| 5,399,146 | 3/1995 | Nowacki et al. | 601/4 |
| 5,409,002 | 4/1995 | Pell | 128/653.1 |
| 5,468,214 | 11/1995 | Hermann et al. | 601/2 |
| 5,470,302 | 11/1995 | Krauss et al. | 601/2 |
| 5,488,951 | 2/1996 | Bauer et al. | 128/653.1 |

FOREIGN PATENT DOCUMENTS

0538659A2  4/1993  European Pat. Off. ........ A61B 17/22
4300740    3/1994  Germany.

Primary Examiner—Marvin M. Lateef
Assistant Examiner—Shawna J. Shaw
Attorney, Agent, or Firm—Edward Blocker

[57] ABSTRACT

A lithotripsy combination, includes a therapy unit and a separate X-ray locating unit which has a first carriage and which can be coupled to the therapy unit via a coupling unit. The X-ray locating unit includes an X-ray source and an X-ray image converter for locating in at least two defined locating positions. Simple alignment of the X-ray locating unit and the therapy unit is achieved in that the therapy unit consists of a second carriage and a shockwave generator which is mounted thereon and which has a stationary focus relative to the carriage, that the two carriages (or parts rigidly connected thereto) can be coupled to one another, via the coupling unit, in such a manner that the coupled carriages can be displaced together and that the focus of the shockwave generator is situated, at least in the locating positions, on the central line which interconnects the X-ray source and the X-ray image converter.

11 Claims, 3 Drawing Sheets

LITHOTRIPSY COMBINATION COMPRISING A THERAPY UNIT

BACKGROUND OF THE INVENTION

1. Field of the Invention

The invention relates to a lithotripsy combination comprising a therapy unit and a separate X-ray locating unit which comprises a first carriage and which can be coupled to the therapy unit via a coupling unit, said X-ray locating unit comprising an X-ray source and X-ray image converter for locating in at least two defined locating positions. A lithotripsy combination of this kind is known from DE-PS 43 00 740.

2. Description of the Related Art

Lithotripsy apparatus are expensive because they must be capable of locating a concrement in a patient arranged on a table, for example by means of an X-ray locating unit, and of crushing the concrement located. Therefore, the known device is based on the idea to use such a lithotripter more economically by also utilizing at least individual components for purposes other than lithotripsy.

To this end, the known lithotripsy combination consists of a therapy unit and a separate X-ray locating unit in the form of a commercially available C-arc which supports an X-ray source and an X-ray image converter and is pivotable about a horizontal axis extending through the C-arc plane. The C-arc is arranged on a carriage and can be used on the one hand for the locating of a concrement in conjunction with the therapy unit and on the other hand, independently from the therapy unit, for a conventional X-ray examination.

The therapy unit of the known device consists of a patient table in which an electroacoustic transducer is integrated, which transducer is pivotable about a horizontal transverse axis and consists of a plurality of piezoelectric elements in a dome-like configuration. This transducer generates ultrasonic waves whose intensity in a focus extending through said pivot axis may become so high that it crushes a concrement present at that area. In order to execute lithotripsy, the carriage with the X-ray locating unit is moved to the therapy unit and the transducer is coupled, via the coupling device, to the C-arc of the X-ray locating unit in such a manner that the C-arc can follow the pivotal motions of the transducer.

In the known lithotripsy combination only coarse alignment can be realized between X-ray locating device and therapy apparatus. For accurate alignment a marker, for example a lead sphere, is positioned in the focus of the transducer so as to appear in the X-ray image, and the C-arc is pivoted to the two locating positions. In the X-ray images formed of the lead sphere in these locating positions an electronic target is moved to the position of the lead sphere and its position is stored. After removal of the lead sphere and arrangement of a patient on the patient table, the setting stored is taken into account for reproducing the electronic target on a monitor displaying the X-ray image.

SUMMARY OF THE INVENTION

It is an object of the invention to make a lithotripsy combination suitable for more universal use; however, alignment of the X-ray locating unit and the therapy unit relative to one another should be substantially easier. This object is achieved in accordance with the invention in that the therapy unit consists of a second carriage and a shockwave generator which is mounted thereon and which has a focus which is stationary relative to the carriage, that the two carriages, or parts rigidly connected thereto, can be coupled to one another via a coupling unit in such a manner that the coupled carriages can be displaced together, and that, at least in the locating positions the focus of the shockwave generator is situated on the central line which interconnects the X-ray source and the X-ray image converter.

In accordance with the invention, the therapy unit thus consists merely of a second carriage and a shockwave generator mounted thereon. The coupling unit couples only the two carriages, or parts permanently connected thereto, so that the X-ray source and the X-ray image converter can be moved (together), independently from the shockwave generator, to the locating positions also when the carriages are coupled to one another. The therapy unit and the X-ray locating unit can be moved together. As a result of the coupling device, they occupy an accurately defined position relative to one another in which the focus of the shockwave generator is situated on the central line interconnecting the X-ray source and the X-ray image converter. Therefore, an additional alignment procedure as in the known lithotripsy combination can be dispensed with.

Whereas in the known lithotripsy combination the locating unit may in principle be an arbitrary commercially available locating unit of the C-arc type, in accordance with the invention the X-ray locating unit and the therapy unit must be adapted to one another from a construction point of view, so that in the coupled condition the focus is always situated on the central line of the locating positions. After uncoupling of the therapy unit, however, the X-ray locating unit can also be used for other X-ray examinations.

It is to be noted that U.S. Pat. No. 5,065,741, notably FIG. 6, already discloses a lithotripsy system which consists of three separate components: a patient table, an X-ray locating unit comprising a C-arc, and a movable therapy unit which comprises a shockwave generator which is also mounted on a C-arc. Without the therapy unit this system can also be used for conventional X-ray examinations. For lithotripsy purposes the lithotripsy unit is arranged against the patient table in such a manner that the X-ray locating unit and the lithotripsy unit are situated to both sides of the table. However, there no facility is provided for alignment of the therapy unit and the X-ray locating unit relative to one another.

In a preferred embodiment of the invention, on the first carriage a C-arc is journalled so as to be pivotable about at least one horizontal axis, which C-arc supports the X-ray source and the X-ray image converter. A C-arc unit can also be universally used for conventional X-ray examinations.

Various possibilities exist as regards X-ray locating by means of such a C-arc unit. A first embodiment utilizes the fact that the C-arc is pivotable to the various locating positions about a horizontal axis which extends parallel to the plane defined by the C-arc, said axis extending through the focus of the shockwave generator in the coupled condition of the two carriages. The lithotripsy combination is then displaced to an examination table, supporting the patient, in such a manner that the pivot axis extends approximately perpendicularly to the longitudinal direction of the table; this pivoting possibility is also used in the known lithotripsy combination.

A second possibility for locating, carried out in a further embodiment of the invention, utilizes the fact that the C-arc is pivotable to at least two locating positions about a horizontal axis which extends perpendicularly to the plane defined by the C-arc, and that in the coupled condition of the two carriages the point of intersection of the central lines coincides with the focus of the shockwave generator in the two locating positions. Thus, in this case the C-arc is pivoted about a second pivot axis which extends approximately parallel to the longitudinal direction of the patient table and on which the center of curvature of the C-arc is situated. This possibility for locating cannot be utilized in the known device, because in the coupled condition the C-arc thereof can no longer be pivoted about this axis. In accordance with the invention, however, such pivoting is readily possible because the coupling device acts on the first carriage, or on a part rigidly connected thereto, but not on the C-arc. Therefore, the latter is pivotable about said second axis, independently from the therapy unit, notably the shockwave generator.

For a lithotripsy treatment the lithotripsy combination is moved to a patient table on which the patient to be treated is arranged. In a preferred embodiment of the invention, the patient table comprises a preferably exchangeable table top which is provided with a cut-out for the lithotripsy combination at a longitudinal side. This is because the shockwave generator on the second carriage is situated, at least substantially, underneath the patient table, so that the shockwave generator can act on the patient through the cut-out (the intermediate space between the shockwave generator and the patient being filled in known manner with a water cushion). After decoupling of the lithotripsy combination and replacement of the table top with the cut-out by a table top without cut-out, the patient table and the X-ray locating unit can be used for conventional X-ray examinations. This is not possible with said known system, because such an examination would be impeded by the electroacoustic transducer for destroying concrements which is arranged underneath the table top.

BRIEF DESCRIPTION OF THE DRAWING

The invention will be described in detail hereinafter with reference to the drawing. Therein.

DETAILED DESCRIPTION OF THE PREFERRED EMBODIMENTS

Figure 1:
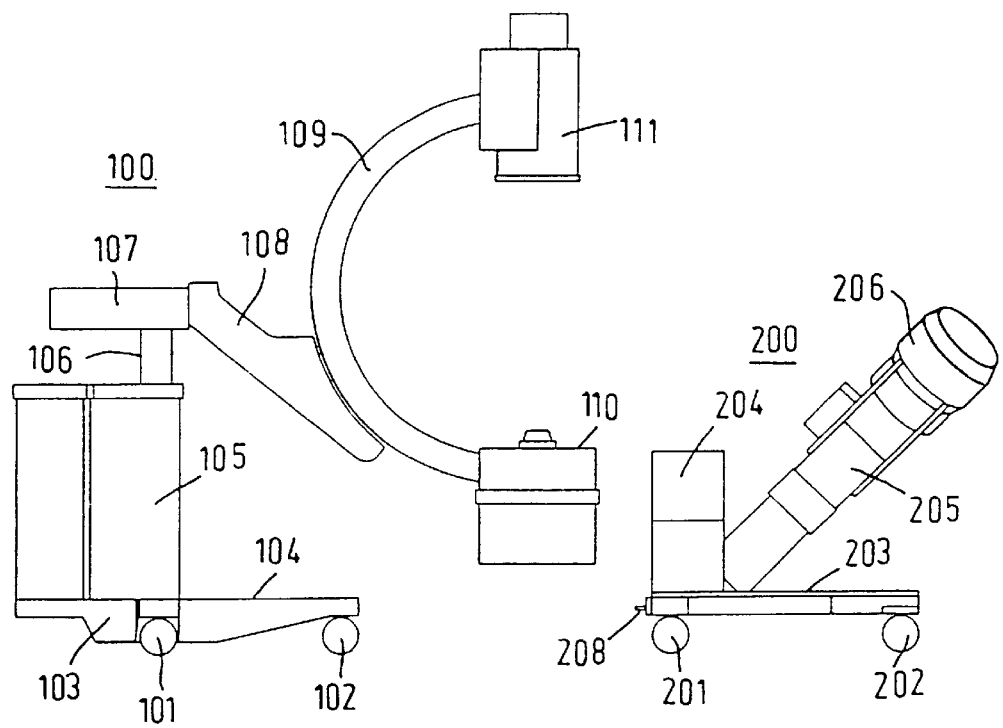
FIG. 1 is a side elevation of the lithotripsy combination in the uncoupled condition.

The reference numeral 100 in FIG. 1 designates the X-ray locating unit and the reference numeral 200 the therapy unit. The X-ray locating unit comprises a carriage 103 which can be displaced on rollers 101 and 102 and which comprises a central portion 104 whereto the front rollers 102 are connected. In the housing 105, provided on the carriage, there are accommodated on the one hand the electrical components for operating the X-ray locating unit and on the other hand a vertical lifting column 106 which is slidable in its longitudinal direction. At its upper end the lifting column supports a horizontal supporting arm 107 in which a guide segment 108 is journalled so as to be pivotable about a horizontal shaft. In the guide segment 108 there is journalled a C-arc 109, one end of which supports an X-ray source 110 whereas its other end supports an X-ray image converter 111, for example an X-ray image intensifier. The C-arc 109 can be pivoted in the guide segment about an axis which extends through its center of curvature (115, FIG. 3), perpendicularly to the plane of drawing of FIG. 1. Moreover, the C-arc can be pivoted, together with the guide segment 108, about a horizontal axis which is situated in the plane of drawing or in the plane which is defined by the C-arc 109, and denoted by the reference numeral 113 in FIG. 3.

The therapy unit 200 also comprises a carriage 203 which is displaceable on rollers 201 and 202 and which supports the shockwave generator. The shockwave generator comprises an electric generator which is accommodated in a housing 204 and a shockwave head 206 which is mounted on an angular support 205. The shockwave head 206 may comprise in known manner a rotation ellipsoid in which an electric discharge, fed by said generator, takes place via a spark gap, which discharge generates shockwaves whose energy is concentrated in one point, i.e. the so-called focus. This focus is situated above the shockwave head 206 in an accurately defined position relative to the carriage 203.

Figure 2:
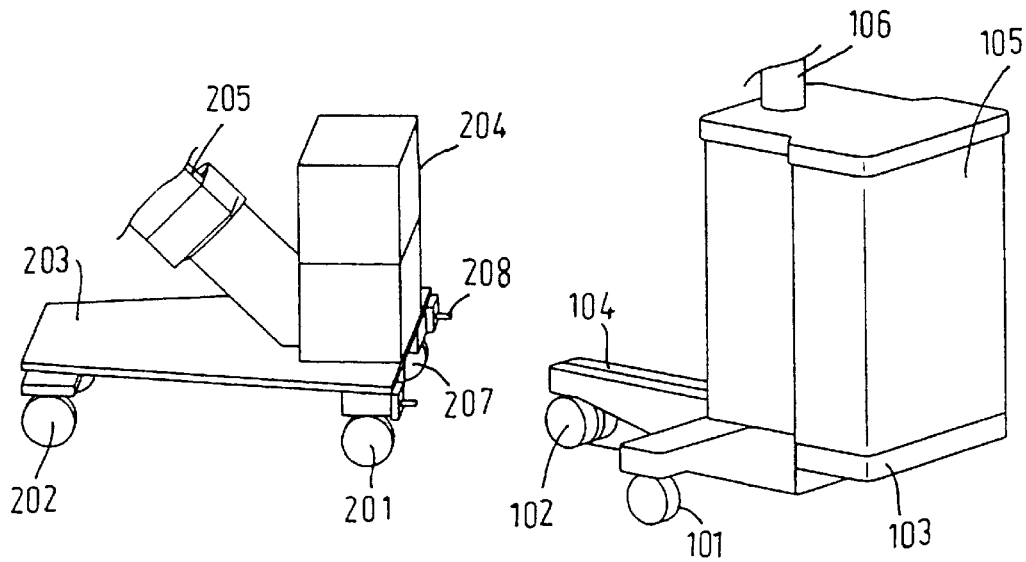
FIG. 2 is a perspective view of parts of the combination shown in FIG. 1.

As appears from FIG. 2, underneath the carriage 203 there is provided a tunnel 207 which serves to receive the central part 104 of the X-ray locating unit 100. When the carriage 103 of the X-ray locating unit is moved to the carriage 203 of the shockwave generator and the central part 104 enters the tunnel, the two carriages are aligned relative to one another in the longitudinal direction; coupling pins 208 on the carriage 203 then engage, at the end of displacement, complementary shaped coupling openings on the carriage 103 which are not shown in detail. When the central part 104 is introduced, the carriage 203 is and the same time lifted slightly so that its rollers 201 and 202 are suspended above the floor. The lithotripsy combination formed by this coupling can then be displaced on the rollers 101 and 102 of the carriage 103. An additional locking device (not shown) can be provided so as to ensure that the coupled condition is maintained.

The coupling unit via which the two carriages 103, 203 can be coupled to one another can also be constructed in a different manner. It is only essential that the two carriages and/or the parts rigidly connected thereto are constructed so that they can be locked or coupled to one another only in an accurately defined position, so as to be displaced together. Carriages 103 and 203 also can be uncoupled (i.e. detached) by first disengaging coupling pins 208 from the complementary shaped coupling openings in the carriage 103 and then removing the central part 104 from the tunnel.

Figure 3:
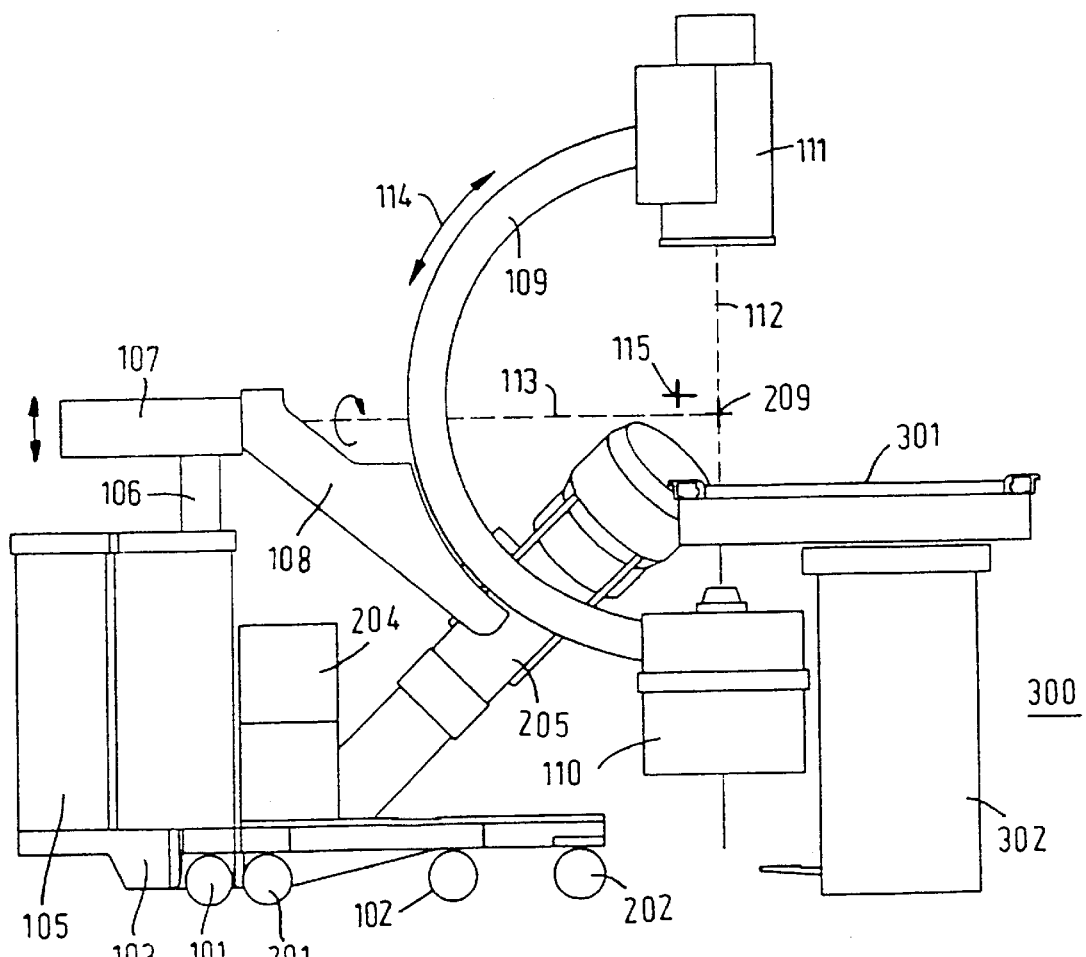
FIG. 3 shows the coupled lithotripsy combination with a patient table.
Figure 5:
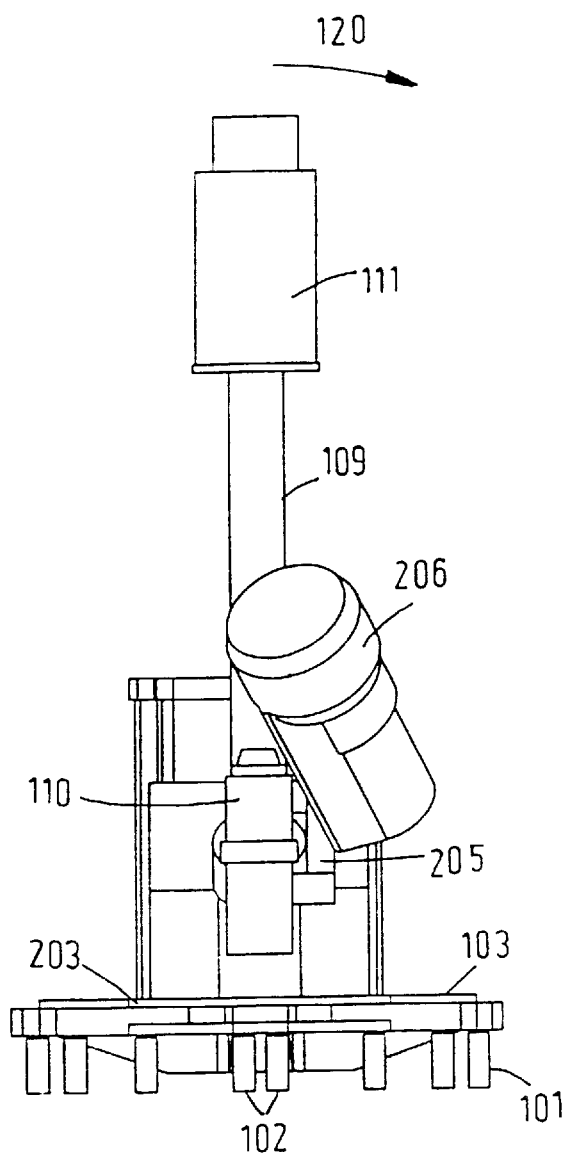
FIG. 5 is a front view of the combination shown in FIG. 3.

FIG. 3 shows the coupled lithotripsy combination together with a patient table 300. As appears notably from FIG. 5, in the vertical position of the C-arc 109 the shockwave head 206 and the support 205 are situated to the side of the C-arc. However, the shockwave head is arranged on the support 205 in such a manner that its focus 209 is situated in the plane of the C-arc, i.e. on the so-called central ray 112 which corresponds to a connecting line between the center of the entrance screen of the X-ray image intensifier 111 and the focal spot emitting the X-rays in the X-ray source 110. If desired, the shockwave head 206 can also be covered by the X-ray beam so as to be imaged on the X-ray image converter 111; however, at least the central ray 112 bypasses the shockwave head.

Figure 4:
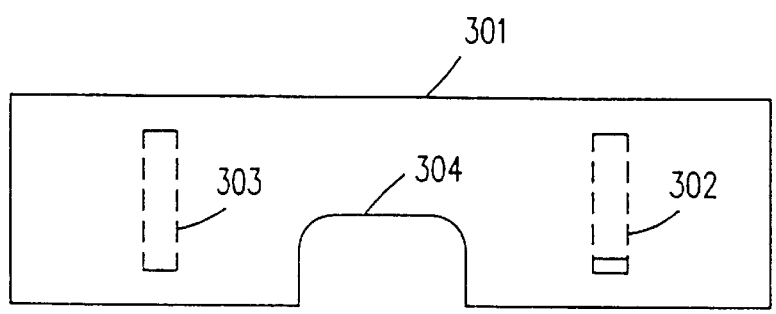
FIG. 4 is a plan view of the patient table.

The patient table 300 comprises a table top 301 and bearing blocks 302 and 303 which enable vertical displacement of the table top 301. Moreover, the table top is constructed as a so-called floating table top, i.e. it can be displaced in its plane. The table top is provided with a cut-out 304 for the shockwave head as shown in FIG. 4. The shockwaves generated in the shockwave head, therefore, can act, via said cut-out and an inflatable watercushion, on a patient arranged on the table top 301, without interacting with the table top.

A first possibility for locating includes pivoting the C-arc 109, together with the guide segment 108, about the horizontal axis 113, situated in the C-arc plane, to a second locating position, i.e. the direction of the arrow 120 (see FIG. 5), through an angle of approximately 30°, during which movement there are no collisions with the measuring head 206 or the support 205. In this second pivotal position the focus 209 must again be situated on the central ray 112. This is achieved when the support 107 on the lifting column 106 is moved to such a position that the pivot axis 113 extends at the same level as the focus 209. The point of intersection of the central ray 112 in the two locating positions then coincides with the focus 209 and is also situated on the pivot axis 113. In order to ensure the correct level of the pivot axis 113, the lifting column 106 should be provided with marks at the relevant height or with a locking position, so that the desired position can be reached in a reproducible manner.

A preferred further possibility for locating includes pivoting, in a perpendicular position of the C-arc, the C-arc 109 within the guide segment 108 about an axis which extends through its center of curvature 115 and perpendicularly to the plane of drawing of FIG. 3, as denoted by the arrow 114. When the center of curvature 115 is situated on the central ray 112 and on the horizontal axis 113, locating by such pivoting, i.e. in arbitrary locating positions, is relatively simply.

However, in many cases the horizontal pivot axis 113 may also not extend through the center of curvature but through the center of gravity of the C-arc unit formed by components 108, 109, 110 and 111, thus enabling manual pivoting about the axis 113. The central ray also may not extend through the center of curvature 115. FIG. 3 shows such a situation in which the center of curvature 115 is situated outside the central ray 112 and outside the pivot axis 113. However, in this case the central rays 112 intersect again in one point in two different locating positions. This point of intersection is coincident with the focus 209 when the lifting column 106 is adjusted to a given height which is usually not coincident with the level at which the pivot axis 113 intersects the focus 209. Therefore, the lifting column 106 must be provided with at least one further mark or locking position so as to enable also locating by pivoting the C-arc about its centre of curvature 115.

This lithotripsy system can also be used to perform conventional X-ray examinations. To this end it is merely necessary to uncouple the therapy unit 200 and to move it to the side and to replace the table top 301 by a table top without a cut-out 304, if necessary. Economic efficiency is improved in that, using the same components, on the one hand lithotripsy treatments can thus be performed and on the other hand X-ray examinations.

It will thus be seen that the objects set forth above and those made apparent from the preceding description are efficiently attained and, since certain changes can be made in the above method and construction set forth without departing from the spirit and scope of the invention, it is intended that all matter contained in the above description and shown in the accompanying drawings shall be interpreted as illustrative and not in a limiting sense.

It is also to be understood that the following claims are intended to cover all the generic and specific features of the invention herein described and all statements of the scope of the invention, which as a matter of language, might be said to fall therebetween.

I claim:

1. A lithotripsy combination, comprising a therapy unit and a separate X-ray locating unit, the X-ray locating unit including a first carriage detachably coupled to the therapy unit via a coupling unit, an X-ray source and an X-ray image converter for locating at least two defined locating positions, the therapy unit including a second carriage and a shockwave generator mounted thereon and having a focus which is stationary relative to the second carriage, the first and second carriages, or parts rigidly connected thereto, detachably coupled to one another via the coupling unit in such manner that when coupled the first and second carriages can be displaced together, and that, at least in the locating positions, a focus of the shockwave generator is situated on a central line which interconnects the X-ray source and the X-ray image converter.

2. The lithotripsy combination as claimed in claim 1, wherein on the first carriage a C-arc is journalled so as to be pivotable about at least one horizontal axis thereto, the C-arc supporting both the X-ray source and the X-ray image converter.

3. The lithotripsy combination as claimed in claim 1, wherein a C-arc is pivotable to the various locating positions about a horizontal axis which extends parallel to the plane defined by the C-arc, said axis extending through the focus of the shockwave generator when the first and second carriages are coupled together.

4. The lithotripsy combination as claimed in claim 2, wherein the C-arc is pivotable to at least two locating positions about a horizontal axis which extends perpendicularly to the plane defined by the C-arc, and wherein when the first and second carriages are coupled together a point of intersection of the central line interconnecting the X-ray source and the X-ray image converter in the two locating positions coincides with the focus of the shockwave generator.

5. A lithotripsy system comprising a patient table and the lithotripsy combination as claimed in claim 1, wherein the patient table comprises an exchangeable table top which is provided with a cut-out for the lithotripsy combination along a longitudinal side of the patient table.

6. The lithotripsy system as claimed in claim 5, wherein the lithotripsy combination further includes on the first carriage a C-arc which is journalled so as to be pivotable about at least one horizontal axis thereto, the C-arc supporting both the X-ray source and the X-ray image converter.

7. The lithotripsy system as claimed in claim 5, wherein the lithotripsy combination further includes a C-arc which is pivotable to the various locating positions about a horizontal axis which extends parallel to the plane defined by the C-arc, said axis extending through the focus of the shockwave generator when the first and second carriages are coupled together.

8. The lithotripsy system as claimed in claim 6, wherein the C-arc is pivotable to at least two locating positions about a horizontal axis which extends perpendicularly to the plane defined by the C-arc, and wherein when the first and second carriages are coupled together a point of intersection of the central line interconnecting the X-ray source and the X-ray image converter in the two locating positions coincides with the focus of the shockwave generator.

9. The lithotripsy combination of claim 5, wherein the first and second carriages, or parts rigidly connected thereto, are detachably coupled to one another via the coupling unit.

10. The lithotripsy combination of claim 7, wherein the first and second carriages, or parts rigidly connected thereto, are detachably coupled to one another via the coupling unit.

11. The lithotripsy combination of claim 8, wherein the first and second carriages, or parts rigidly connected thereto, are detachably coupled to one another via the coupling unit.

* * * * *